United States Patent
Mitamura

(10) Patent No.: US 11,864,733 B2
(45) Date of Patent: Jan. 9, 2024

(54) SPIRAL TUBE AND ENDOSCOPE

(71) Applicant: OLYMPUS CORPORATION, Tokyo (JP)

(72) Inventor: Yuki Mitamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 721 days.

(21) Appl. No.: 17/080,225

(22) Filed: Oct. 26, 2020

(65) Prior Publication Data

US 2021/0113070 A1   Apr. 22, 2021

Related U.S. Application Data

(63) Continuation of application No. PCT/JP2019/017997, filed on Apr. 26, 2019.

(30) Foreign Application Priority Data

Apr. 26, 2018 (JP) ................. 2018-085744

(51) Int. Cl.
*A61B 1/00* (2006.01)
*A61M 25/01* (2006.01)

(52) U.S. Cl.
CPC ........ *A61B 1/00154* (2013.01); *A61B 1/0016* (2013.01); *A61M 25/0113* (2013.01)

(58) Field of Classification Search
CPC ............ A61B 1/00147; A61B 1/00154; A61B 1/00156; A61B 1/0016; A61B 1/00135; A61B 1/0014

See application file for complete search history.

(56) References Cited

U.S. PATENT DOCUMENTS

| | | |
|---|---|---|
| 2007/0059956 A1 | 3/2007 | Kura et al. |
| 2007/0060790 A1 | 3/2007 | Kura et al. |
| 2007/0080962 A1 | 4/2007 | Kura et al. |

(Continued)

FOREIGN PATENT DOCUMENTS

| | | |
|---|---|---|
| JP | 2008284161 A1 | 9/2016 |
| WO | WO 2005/110197 A1 | 11/2005 |
| WO | WO 2014/069424 A1 | 5/2014 |

OTHER PUBLICATIONS

International Search Report dated Jul. 9, 2019 issued in PCT/JP2019/017997.

*Primary Examiner* — Timothy J Neal
(74) *Attorney, Agent, or Firm* — Scully, Scott, Murphy & Presser, P.C.

(57) ABSTRACT

A spiral tube is provided rotatably around an insertion axis of the insertion portion by a driving force of a driving unit, and includes a first cylindrical member formed into a cylindrical shape, a second cylindrical member provided at another end, and formed into a cylindrical shape, an outer layer tube that has one end fixed to the first cylindrical member, and has an longitudinal axis, an inner layer tube that has one end fixed to the second cylindrical member, and is covered with the outer layer tube so that the outer layer tube is slidable in a direction along the longitudinal axis, and a holding member provided on the outer layer tube, and configured to restrict movement of the outer layer tube with respect to the inner layer tube to a predetermined range, and to hold the inner layer tube in the outer layer tube.

7 Claims, 8 Drawing Sheets

(56) References Cited

U.S. PATENT DOCUMENTS

2013/0035552 A1\* 2/2013 Moriyama ............... A61B 1/31
   600/149
2015/0133856 A1\* 5/2015 Nishiie .............. A61B 1/00135
   604/95.01

\* cited by examiner

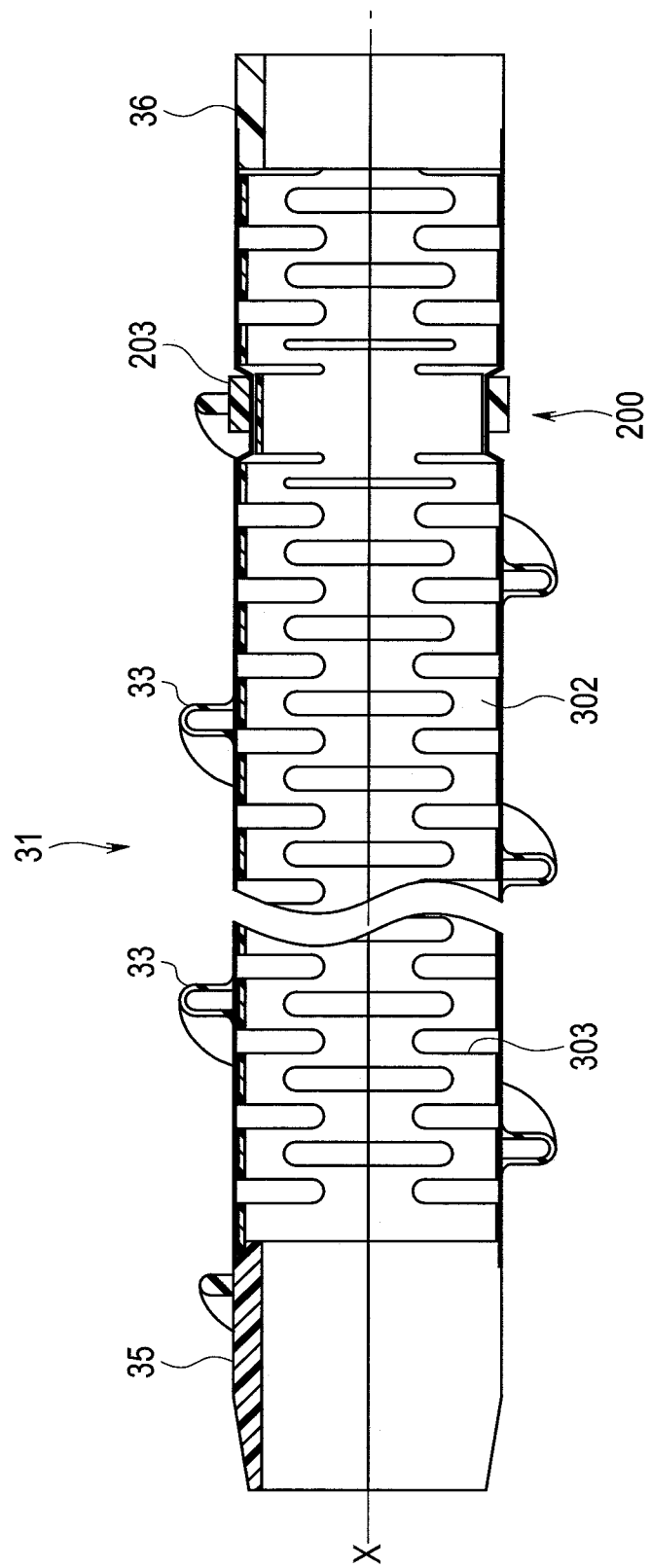

US 11,864,733 B2

SPIRAL TUBE AND ENDOSCOPE

CROSS REFERENCE TO RELATED APPLICATION

This application is a continuation application of PCT/JP2019/017997 filed on Apr. 26, 2019 and claims benefit of Japanese Application No. 2018-085744 filed in Japan on Apr. 26, 2018, the entire contents of which are incorporated herein by this reference.

BACKGROUND OF THE INVENTION

1. Field of the Invention

The present invention relates to a spiral tube configured to be disposed on an insertion portion of an endoscope to drive rotationally, and the endoscope.

2. Description of the Related Art

Endoscopes are used in a medical field, an industrial field and the like.

It is possible to perform observation, examination, treatment or the like with an endoscope for medical use by inserting an insertion portion into a body that is a subject. An endoscope generally has an insertion portion, an operation portion, and a universal cord. In a configuration having a bending portion and a flexible tube portion in the insertion portion, the insertion portion is inserted into a digestive organ and a digestive tract that are body cavities transanally, orally or nasally.

In an endoscope, the flexible tube portion of the insertion portion has flexibility. When a user inserts the insertion portion into an intestinal tract, for example, the user inserts the insertion portion located outside the body toward an intestinal tract deep part by performing a twist operation or a feed operation, while bending the bending portion by operating the bending operation knob provided at the operation portion.

However, the twist operation or the feed operation is a technique to insert the insertion portion smoothly toward the deep part of a body cavity, and requires skill. Accordingly, for an endoscope, as an auxiliary configuration that causes the insertion portion to advance to and retreat from a deep part, there is well known a spiral unit or the like having a spiral tube that rotates around the longitudinal axis of the insertion portion by receiving the driving force from a motor, as disclosed in International Publication No. WO 2014-069424, for example.

In the conventional spiral unit for an endoscope disclosed in International Publication No. WO 2014-069424, a spiral tube is configured by a plurality of layers, and the plurality of layers are bonded and fixed.

SUMMARY OF THE INVENTION

A spiral tube in one aspect of the present invention is a spiral tube configured to be disposed on an outer peripheral portion of an insertion portion of an endoscope configured to be inserted into a subject, and rotatable around an insertion axis of the insertion portion by a driving force of a driving unit, and includes a first cylindrical member provided at one end and formed into a cylindrical shape, a second cylindrical member provided at another end and formed into a cylindrical shape, an outer layer tube that has one end fixed to the first cylindrical member, and includes a longitudinal axis, an inner layer tube that has one end fixed to the second cylindrical member, and is covered with the outer layer tube so that the outer layer tube is slidable in a direction along the longitudinal axis, a holding member provided at another end side that is an opposite side to the one end of the outer layer tube and configured to restrict movement of the outer layer tube with respect to the inner layer tube to a predetermined range and to hold the inner layer tube in the outer layer tube, a circumferential groove in a recessed portion shape that is provided at a position where the holding member is provided, of the inner layer tube, and a ring member provided on the holding member, and placed on an outer peripheral part of the outer layer tube that covers the circumferential groove.

An endoscope in one aspect of the present invention includes a spiral tube that is configured to be disposed on an outer peripheral portion of an insertion portion of an endoscope configured to be inserted into a subject, is rotatable around an insertion axis of the insertion portion by a driving force of a driving unit, and includes a first cylindrical member provided at one end and formed into a cylindrical shape, a second cylindrical member provided at another end and formed into a cylindrical shape, an outer layer tube that has one end fixed to the first cylindrical member, and includes a longitudinal axis, an inner layer tube that has one end fixed to the second cylindrical member, and is covered with the outer layer tube so that the outer layer tube is slidable in a direction along the longitudinal axis, a holding member provided at another end side that is an opposite side to the one end of the outer layer tube, and configured to restrict movement of the outer layer tube with respect to the inner layer tube to a predetermined range and to hold the inner layer tube in the outer layer tube, a circumferential groove in a recessed portion shape that is provided at a position where the holding member is provided, of the inner layer tube, and a ring member provided on the holding member, and placed on an outer peripheral part of the outer layer tube that covers the circumferential groove.

BRIEF DESCRIPTION OF THE DRAWINGS

FIG. 10 is a sectional view illustrating a configuration of a spiral tube of a second modification, according to one aspect of the present invention.

DETAILED DESCRIPTION OF THE PREFERRED EMBODIMENT

Figure 1:
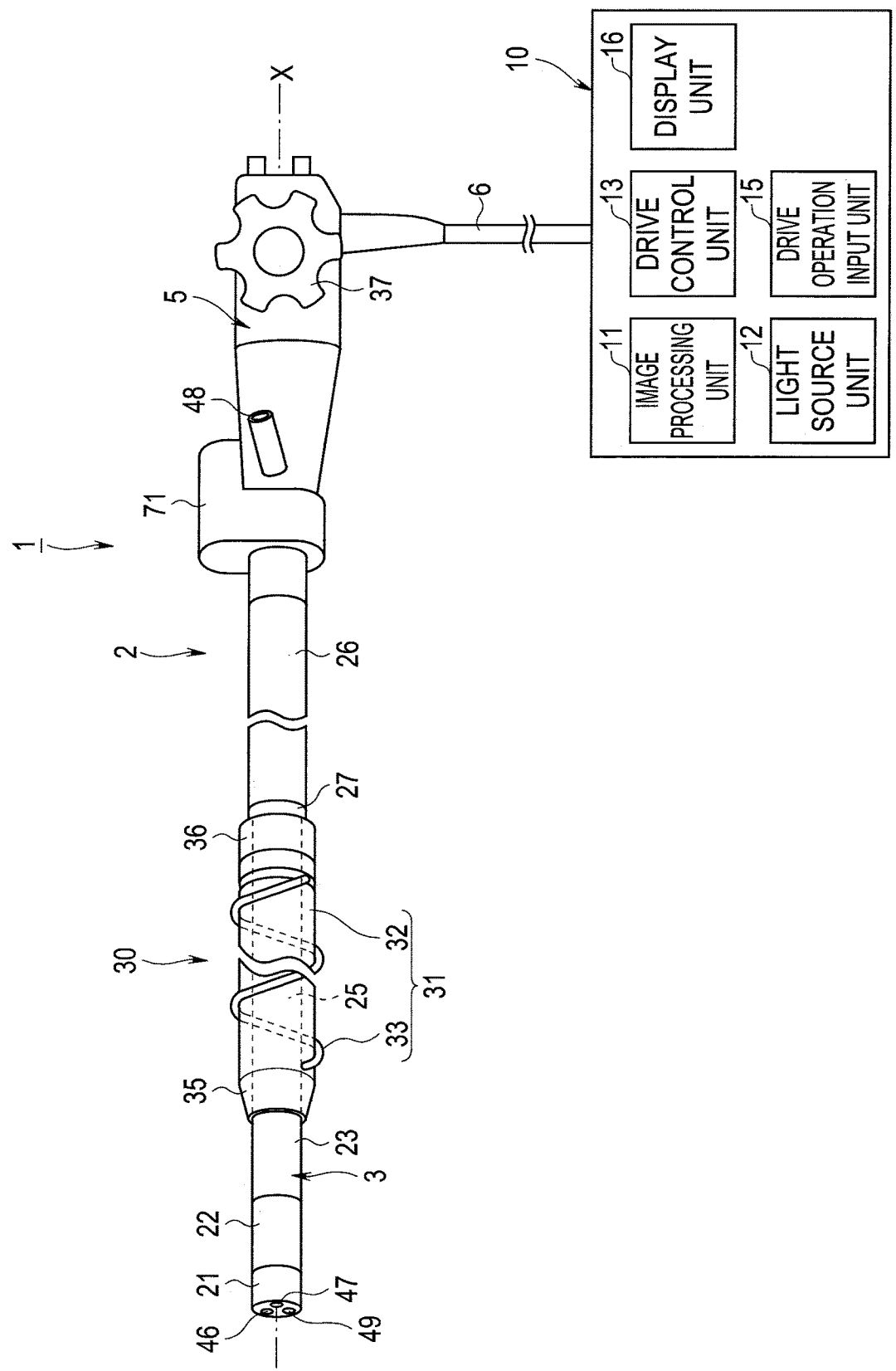
FIG. 1 illustrates an endoscope apparatus that is an insertion apparatus, according to one aspect of the present invention.

Hereinafter, an embodiment of the present invention will be described with reference to the drawings.

Note that in the respective drawings that are used in the following explanation, a scale may differ for each of components so that the respective components have such sizes that the respective components are recognizable on the drawings. In other words, the present invention is not limited to only numbers and quantities of the components, shapes of the components, ratios of sizes of the components, and relative positional relationships of the respective components that are illustrated in the drawings.

The embodiment of the present invention will be described with reference to FIG. 1 to FIG. 6.

Figure 2:
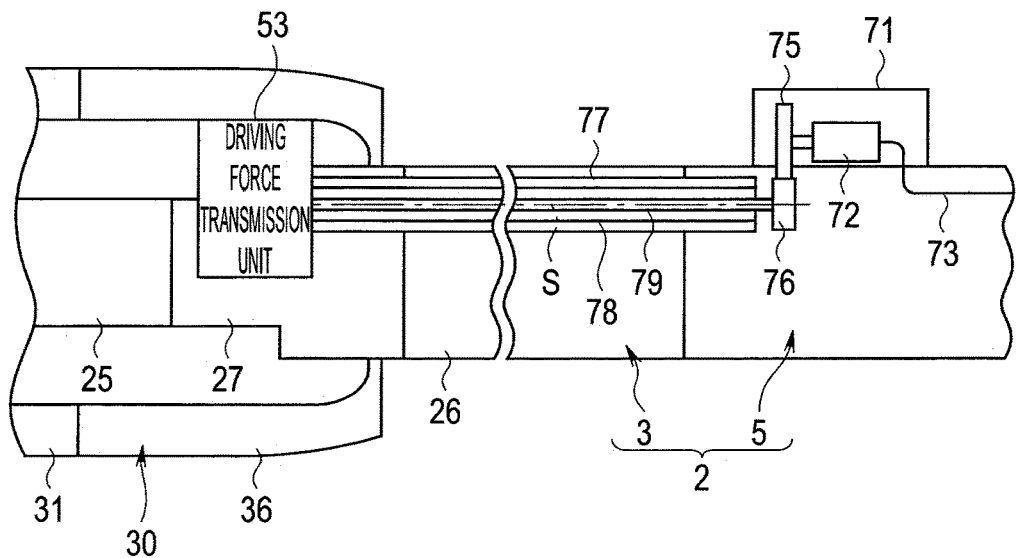
FIG. 2 is a view illustrating a configuration that transmits a rotational driving force to a rotation unit, according to one aspect of the present invention.
Figure 3:
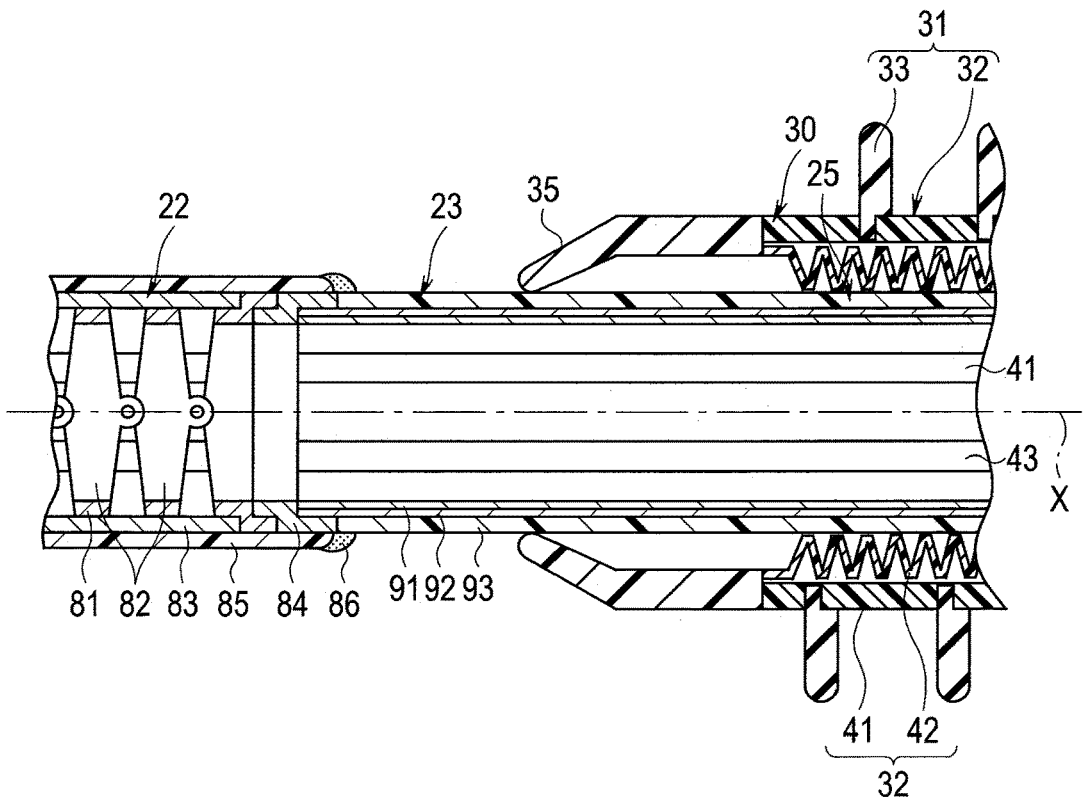
FIG. 3 is a view illustrating configurations of a bending portion, a first flexible tube portion, a second flexible tube portion and the rotation unit, according to one aspect of the present invention.
Figure 4:
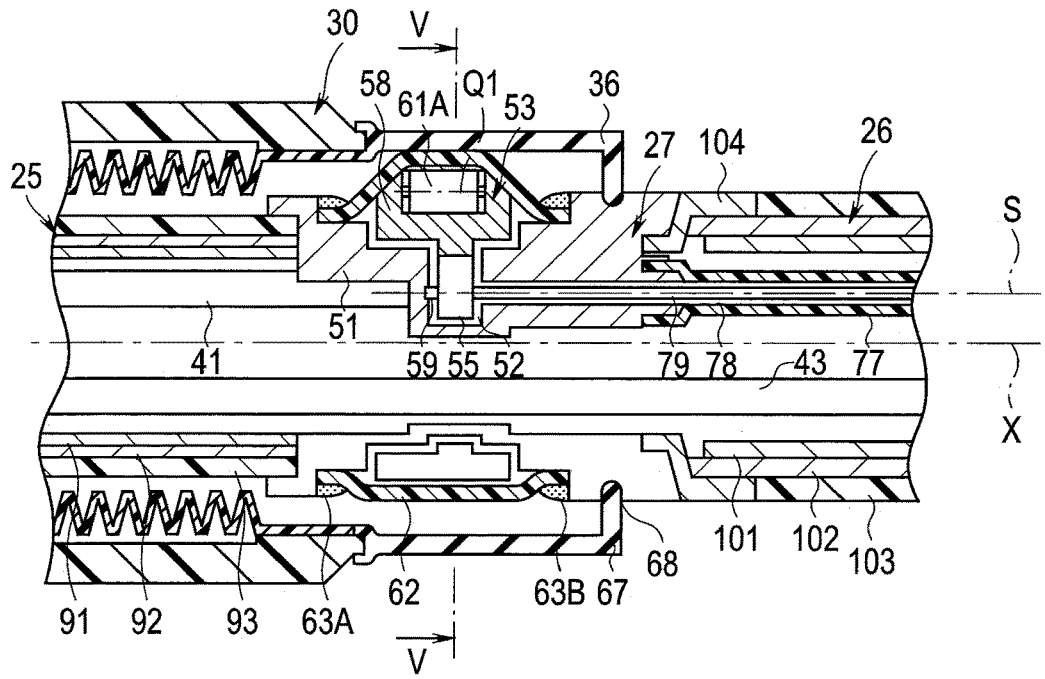
FIG. 4 is a view illustrating configurations of the second flexible tube portion, a third flexible tube portion, a base portion and the rotation unit, according to one aspect of the present invention.
Figure 5:
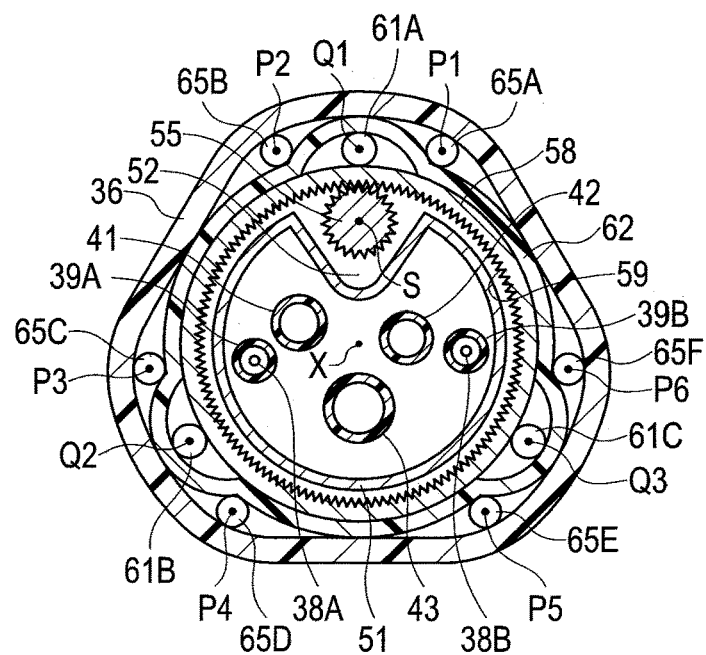
FIG. 5 is a sectional view along a V-V line in FIG. 4, according to one aspect of the present invention.
Figure 6:
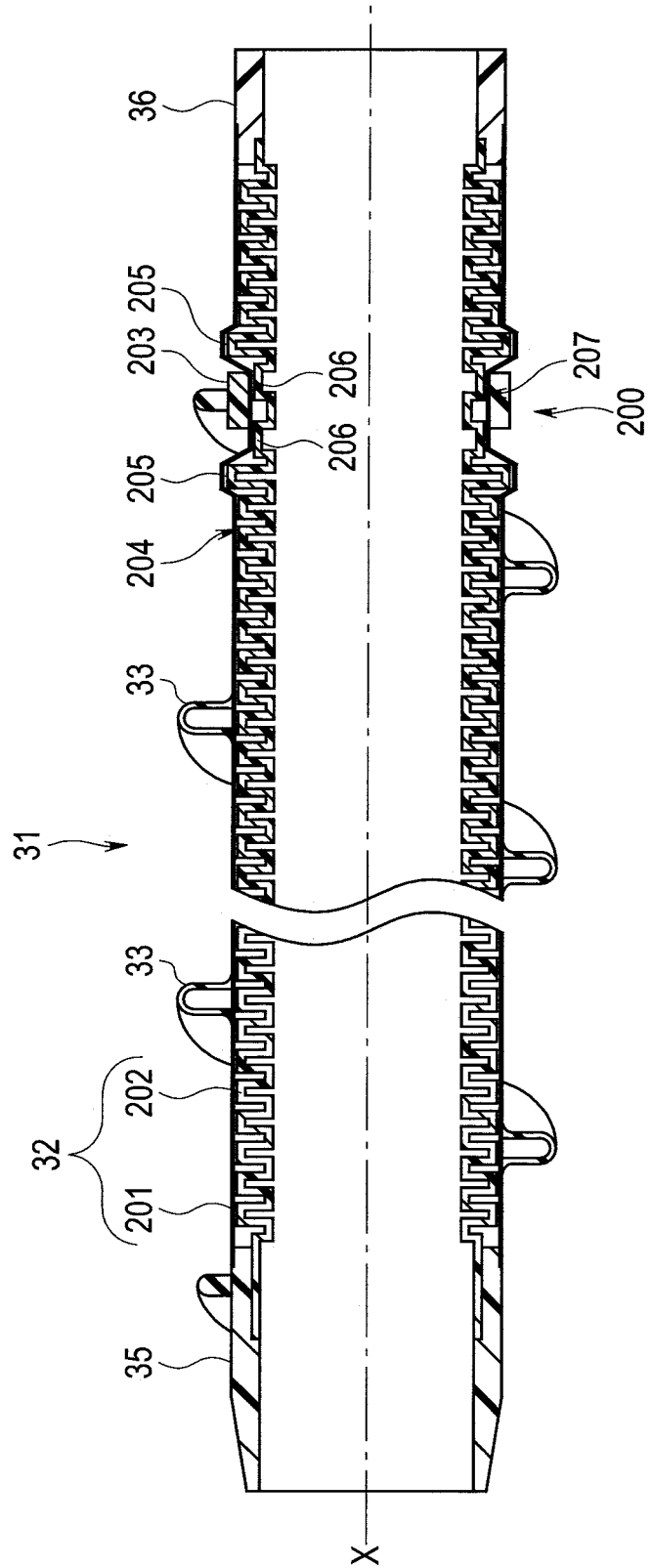
FIG. 6 is a sectional view illustrating a configuration of a spiral tube, according to one aspect of the present invention.
Figure 7:
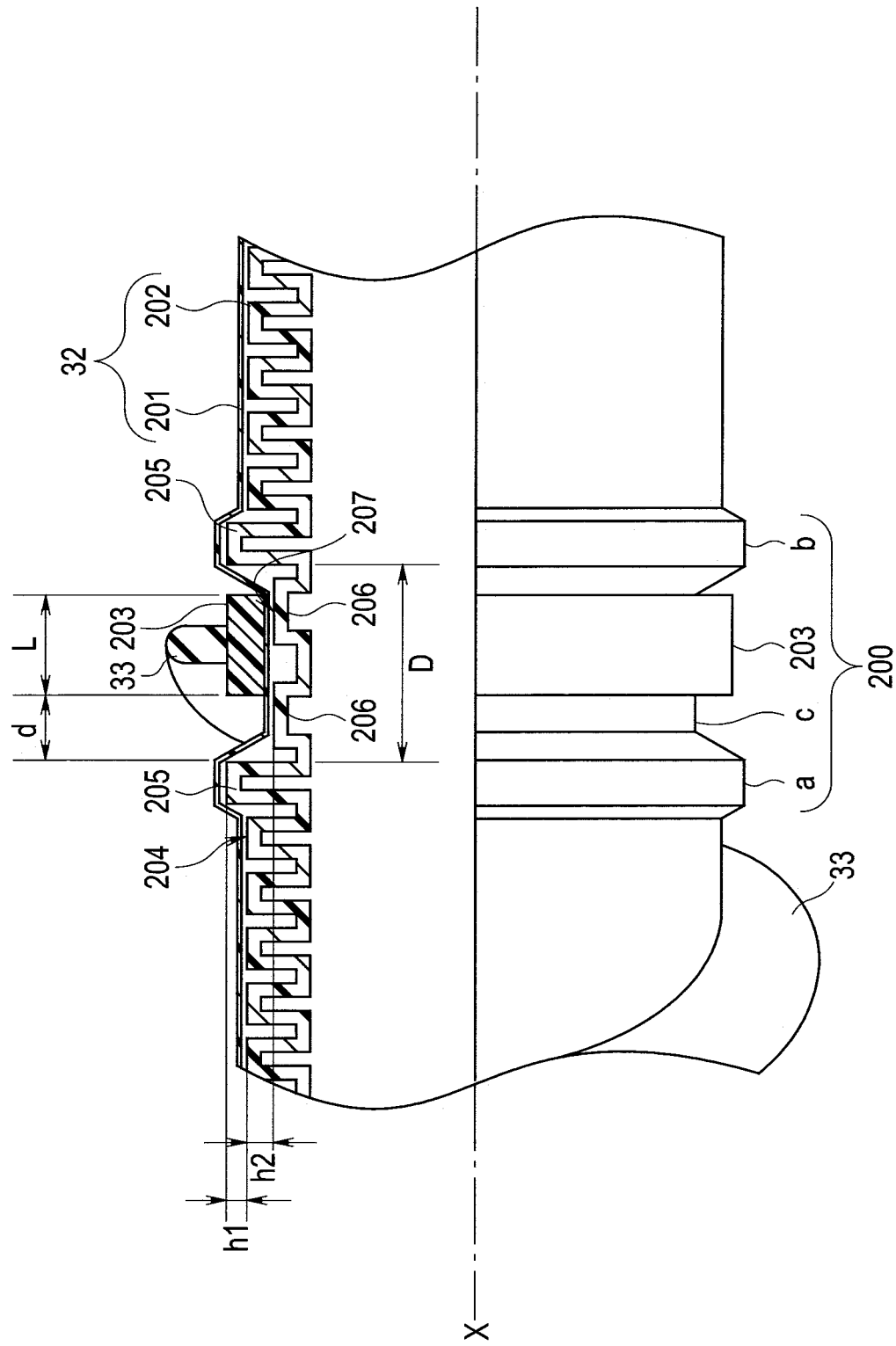
FIG. 7 is a partial sectional view illustrating a configuration of a sliding range restriction portion of the spiral tube, according to one aspect of the present invention.
Figure 8:
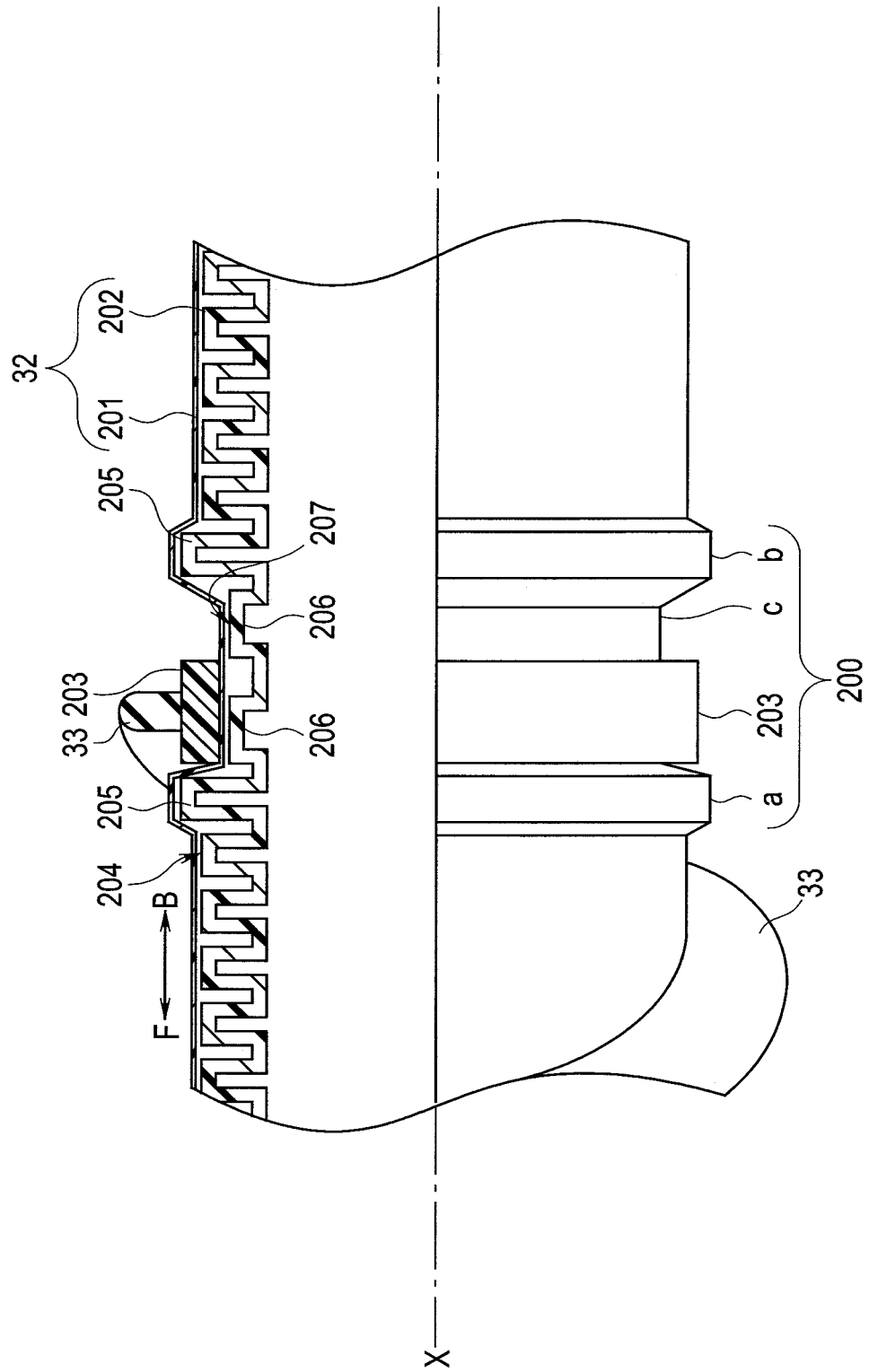
FIG. 8 is a partial sectional view of the sliding range restriction portion of the spiral tube with an outer sheath moving to a distal end side, according to one aspect of the present invention.

The embodiment of an endoscope apparatus that is an insertion apparatus of one aspect of the present invention will be described with reference to the drawings. FIG. 1 illustrates the endoscope apparatus that is the insertion apparatus. FIG. 2 is a view illustrating a configuration that transmits a rotational driving force to a rotation unit. FIG. 3 is a view illustrating configurations of a bending portion, a first flexible tube portion, a second flexible tube portion and the rotation unit. FIG. 4 is a view illustrating configurations of the second flexible tube portion, a third flexible tube portion, a base portion and the rotation unit. FIG. 5 is a sectional view along a V-V line in FIG. 4. FIG. 6 is a sectional view illustrating a configuration of a spiral tube. FIG. 7 is a partial sectional view illustrating a configuration of a sliding range restriction portion of the spiral tube. FIG. 8 is a partial sectional view of the sliding range restriction portion of the spiral tube with an outer sheath moving to a distal end side.

As illustrated in FIG. 1, an endoscope apparatus 1 has a longitudinal axis X that is an insertion axis. Explanation will be made hereinafter, with an extension side of an insertion portion 3 set as a distal end direction, and an operation portion 5 side that is in an opposite direction to the distal end direction set as a proximal end direction. The extension side of the insertion portion 3 is one side in a direction parallel with the longitudinal axis X of an endoscope 2. The distal end direction and the proximal end direction are axial parallel directions parallel with the longitudinal axis X.

The endoscope apparatus 1 includes the endoscope 2 that is an insertion apparatus. The endoscope 2 includes the insertion portion (endoscope insertion portion) 3 that is provided extensively along the longitudinal axis X, an operation portion (endoscope operation portion) 5 that is provided at a proximal end direction side from the insertion portion 3, and a peripheral unit 10.

Note that the peripheral unit 10 includes an image processing unit 11 such as an image processor, a light source unit 12 including a light source such as a lamp, a drive control unit 13 that is a control apparatus including, for example, a power supply, a storage unit such as a memory, and a CPU or an ASIC, a drive operation input unit 15 that is a button, a foot switch and the like, and a display unit 16 such as a monitor.

The insertion portion 3 of the endoscope 2 is provided to extend along the longitudinal axis X, and is inserted into a body cavity at a time of use of the endoscope apparatus 1. The insertion portion 3 includes a distal end configuration portion 21 forming a distal end of the insertion portion 3, a bending portion 22 that is provided at a proximal end direction side from the distal end configuration portion 21, a first flexible tube portion 23 that is provided at a proximal end direction side from the bending portion 22, a second flexible tube portion 25 that is provided at a proximal end direction side from the first flexible tube portion 23, and a third flexible tube portion 26 that is provided at a proximal end direction side from the second flexible tube portion 25.

A base portion 27 is provided in a space along the axial parallel direction parallel with the longitudinal axis X between the second flexible tube portion 25 and the third flexible tube portion 26. The second flexible tube portion 25 is connected to the third flexible tube portion 26 via the base portion 27.

Here, in a section orthogonal to the longitudinal axis X, a direction to be away from the longitudinal axis X is set as an outer peripheral direction (de-axial direction), and a center direction toward the longitudinal axis X is an inner peripheral direction (adaxial direction).

On the insertion portion 3, a rotation unit 30 that is of a disposal (throwaway) type here and is cylindrical is provided on an outer peripheral direction side. In other words, in a state where the insertion portion 3 is inserted through the rotation unit 30, the rotation unit 30 is fitted onto the second flexible tube portion 25.

In the endoscope 2, the rotation unit 30 rotates around the longitudinal axis X with respect to the insertion portion 3 by a rotational driving force being transmitted to the rotation unit 30, in the state where the rotation unit 30 is fitted on the insertion portion 3.

The rotation unit 30 includes a spiral tube 31 that is provided to extend along the longitudinal axis X. The spiral tube 31 includes a tube portion 32, and a spiral fin 33 provided on an outer peripheral surface of the tube portion 32.

The spiral fin 33 is provided spirally with the longitudinal axis X as a center from the proximal end direction to the distal end direction. A distal end side cylindrical portion 35 is provided at a distal end direction side of the spiral tube 31 in the rotation unit 30.

The distal end side cylindrical portion 35 is formed into a taper shape in which an outside diameter becomes smaller toward a distal end direction side. A cylindrical proximal end side cylindrical portion 36 is provided at a proximal end direction side of the spiral tube 31.

In a state where the spiral fin 33 of the spiral tube 31 is pressed in the inner peripheral direction by a body cavity wall or the like, the rotation unit 30 rotates around the longitudinal axis X, and thereby a propulsive force in the distal end direction or the proximal end direction acts on the insertion portion 3 and the rotation unit 30.

In other words, movability in the insertion direction (distal end direction) of the insertion portion 3 in the body cavity such as an inside of a small intestine, or an inside of a large intestine is enhanced by the propulsive force in the distal end direction, and mobility in an extraction direction (proximal end direction) of the insertion portion 3 in the body cavity is enhanced by the propulsive force in the proximal end direction.

One end of a universal cord 6 is connected to the operation portion 5 of the endoscope 2. The other end of the universal cord 6 is connected to the peripheral unit 10. On an outer surface of the operation portion 5, a bending operation knob 37 to which a bending operation of the bending portion 22 is inputted is provided.

On the outer surface of the operation portion 5, a treatment instrument insertion portion 48 in which a treatment instrument such as forceps is inserted is provided. The treatment instrument insertion portion 48 communicates with a channel tube 43 (refer to FIG. 3) placed in the insertion portion 3.

In other words, the channel tube 43 passes through an inside of the insertion portion 3 and an inside of the operation portion 5, and has one end connected to the treatment instrument insertion portion 48. The treatment instrument that is inserted from the treatment instrument insertion portion 48 passes through an inside of the channel tube 43, and protrudes in the distal end direction from an opening portion 49 of the distal end configuration portion 21. Subsequently, a treatment by the treatment instrument is performed in a state where the treatment instrument protrudes from the opening portion 49 of the distal end configuration portion 21.

A motor housing 71 is connected to the operation portion 5. A motor 72 (refer to FIG. 2) that is a driving source is housed inside of the motor housing 71.

One end of a motor cable 73 is connected to the motor 72 housed in the motor housing 71 provided at the operation portion 5 as illustrated in FIG. 2. The motor cable 73 is provided to extend through the inside of the operation portion 5 and an inside of the universal cord 6, and the other end is connected to the drive control unit 13 of the peripheral unit 10.

The motor 72 drives by being provided with electric power from the drive control unit 13 via the motor cable 73. A rotational driving force that rotates the rotation unit 30 is generated by the motor 72 being driven. A relay gear 75 is attached to the motor 72. A drive gear 76 configured to be meshed with the relay gear 75 is provided at the inside of the operation portion 5.

As illustrated in FIG. 3, at the inside of the insertion portion 3, an image pickup cable 41, a light guide (not illustrated), and the aforementioned channel tube 43 are provided to extend along the longitudinal axis X.

The bending portion 22 of the insertion portion 3 includes a bending tube 81. The bending tube 81 includes a plurality of metal bending pieces 82.

The respective bending pieces 82 are connected rotatably to the adjacent bending pieces 82. In the bending portion 22, an outer peripheral direction side of the bending tube 81 is covered with a bending net-shaped tube 83 that is a bending braid. In the bending net-shaped tube 83, metal element wires (not illustrated) are woven into a net shape.

In the bending portion 22, an outer peripheral direction side of the bending net-shaped tube 83 is covered with a bending outer sheath 85. The bending outer sheath 85 is formed of a fluororubber, for example.

An image pickup device (not illustrated) configured to pick up an image of an object is provided inside of the distal end configuration portion 21 (distal end portion) of the insertion portion 3. The image pickup device performs image pickup of an object through an observation window 46 provided in the distal end configuration portion 21 of the endoscope 2, illustrated in FIG. 1.

One end of the image pickup cable 41 is connected to the image pickup device. The image pickup cable 41 is provided to extend through the inside of the insertion portion 3, the inside of the operation portion 5 and the inside of the universal cord 6, and the other end is connected to the image processing unit 11 of the peripheral unit 10 illustrated in FIG. 1.

The image processing unit 11 performs image processing of an object image that is picked up, and generates an image of the object. Subsequently, the generated image of the object is displayed on the display unit 16 (refer to FIG. 1).

The light guide 42 is provided to extend through the inside of the insertion portion 3, the inside of the operation portion 5, and the inside of the universal cord 6, and is connected to the light source unit 12 of the peripheral unit 10. A light emitted from the light source unit 12 is guided by the light guide 42, and is irradiated to the object from an illumination window 47 of the distal end portion (distal end configuration portion 21) of the insertion portion 3 illustrated in FIG. 1.

As illustrated in FIG. 4, a support member 51 formed from a metal is provided at the base portion 27. A proximal end portion of the second flexible tube portion 25 is connected to a distal end portion of the support member 51.

A distal end portion of the third flexible tube portion 26 is connected to a proximal end portion of the support member 51. Thereby, the second flexible tube portion 25 and the third flexible tube portion 26 are connected via the base portion 27.

As illustrated in FIG. 4 and FIG. 5, in the base portion 27, a cavity portion 52 is defined by the support member 51. A driving force transmission unit 53 is attached to the support member 51.

The driving force transmission unit 53 is disposed in the cavity portion 52. The driving force transmission unit 53 is driven by a rotational driving force that rotates the rotation unit 30 being transmitted to the driving force transmission unit 53. The driving force transmission unit 53 includes a drive gear 55.

The driving force transmission unit 53 includes a rotating cylindrical member 58. The rotating cylindrical member 58 is attached to the base portion 27 in a state where the support member 51 is inserted through the rotating cylindrical member 58. The rotating cylindrical member 58 is rotatable around the longitudinal axis X with respect to the insertion portion 3 (base portion 27).

Here, two directions in which the rotation unit 30 rotates are directions around the longitudinal axis X. An inner peripheral gear portion 59 is provided throughout an entire periphery with respect to the direction around the longitudinal axis X, on an inner peripheral surface of the rotating cylindrical member 58. The inner peripheral gear portion 59 is meshed with the drive gear 55.

In the present embodiment, three inner rollers 61A to 61C are attached to the rotating cylindrical member 58. The inner rollers 61A to 61C are respectively disposed to be separated from one another by predetermined intervals in the direction around the longitudinal axis X.

The respective inner rollers 61A to 61C have corresponding roller axes Q1 to Q3. The respective inner rollers 61A to 61C are rotatable with respect to the rotating cylindrical member 58 with the corresponding roller axes Q1 to Q3 as centers.

The inner rollers 61A to 61C are respectively rotatable around the longitudinal axis with respect to the insertion portion 3 (base portion 27) integrally with the rotating cylindrical member 58.

Outer peripheral direction sides of the rotating cylindrical member 58 and the inner rollers 61A to 61C are covered with a cylindrical cover member 62. A distal end of the cover member 62 is fixed to an outer peripheral surface of the support member 51 via an adhesive portion 63A such as an adhesive, and a proximal end of the cover member 62 is fixed to the outer peripheral surface of the support member 51 via an adhesive portion 63B such as an adhesive.

The cavity portion 52 in which the driving force transmission unit 53 is disposed is partitioned from an outside of the insertion portion 3 by the cover member 62. At a fixing position of the distal end of the cover member 62, and a fixing position of the proximal end of the cover member 62, a space between the support member 51 and the cover member 62 is held with watertightness.

Thereby, a liquid is prevented from flowing from the outside of the insertion portion 3 to the cavity portion 52 and the driving force transmission unit 53. At sites where the inner rollers 61A to 61C are located, the cover member 62 protrudes in the outer peripheral direction, in the direction around the longitudinal axis X.

Note that the cover member 62 is fixed to the insertion portion 3, and the rotating cylindrical member 58 and the inner rollers 61A to 61C are respectively rotatable around the longitudinal axis X with respect to the cover member 62.

As illustrated in FIG. 5, six outer rollers 65A to 65F are attached to an inner peripheral surface of the proximal end side cylindrical portion 36. The outer rollers 65A to 65F are located at the outer peripheral direction side of the cover member 62.

In a state where the rotation unit 30 is fitted to the insertion portion 3, in the direction around the longitudinal axis X, the inner roller 61A is located between the outer roller 65A and the outer roller 65B, and the inner roller 61B is located between the outer roller 65C and the outer roller 65D.

Further, in the direction around the longitudinal axis X, the inner roller 61C is located between the outer roller 65E and the outer roller 65F. The respective outer rollers 65A to 65F have corresponding roller axes P1 to P6.

The respective outer rollers 65A to 65F are rotatable with respect to the cover member 62 and the proximal end side cylindrical portion 36 with the corresponding roller axes P1 to P6 as centers. The outer rollers 65A to 65F are rotatable around the longitudinal axis X with respect to the insertion portion 3 (base portion 27) integrally with the rotation unit 30.

By being configured in this way, the rotating cylindrical member 58 rotates around the longitudinal axis X when the driving force transmission unit 53 is driven by the rotational driving force. Thereby, the inner roller 61A presses the outer roller 65A or the outer roller 65B.

Likewise, the inner roller 61B presses the outer roller 65C or the outer roller 65D, and the inner roller 61C presses the outer roller 65E or the outer roller 65F.

Thereby, the driving force is transmitted from the inner rollers 61A to 61C to the outer rollers 65A to 65F of the rotation unit 30, and the rotation unit 30 rotates with the longitudinal axis X as a center with respect to the insertion portion 3 and the cover member 62.

As described above, the outer rollers 65A to 65F that are attached to the proximal end side cylindrical portion 36 configure a driving force receiving unit that receives a rotational driving force from the driving force transmission unit 53 that is driven.

The outer rollers 65A to 65F that are the driving force receiving unit are provided at the proximal end direction side from the spiral tube 31. In the state where the rotation unit 30 is fitted to the insertion portion 3, the outer rollers 65A to 65F are located at the outer peripheral direction side of the base portion 27.

Since the respective inner rollers 61A to 61C rotate with the corresponding roller axes Q1 to Q3 as the centers, frictions between the respective inner rollers 61A to 61C and the cover member 62 decrease.

Likewise, since the respective outer rollers 65A to 65F rotate with the corresponding roller axes P1 to P6 as the centers, frictions between the respective outer rollers 65A to 65F and the cover member 62 decrease.

Therefore, the rotational driving force is properly transmitted to the rotation unit 30 from the inner rollers 61A to 61C, and the rotation unit 30 properly rotates.

Note that a locking claw 67 that protrudes in the inner peripheral direction is provided at the proximal end side cylindrical portion 36. In the support member 51 of the base portion 27, a locking groove 68 is provided throughout an entire periphery in the direction around the longitudinal direction.

The locking claw 67 is locked to the locking groove 68, whereby movement along the longitudinal axis X of the rotation unit 30 with respect to the insertion portion 3 is restricted. However, in a state where the locking claw 67 is locked to the locking groove 68, the locking claw 67 is movable in the direction around the longitudinal axis with respect to the locking groove 68.

As illustrated in FIG. 2 and FIG. 4, inside of the third flexible tube portion 26 of the insertion portion 3, the guide tube 77 is provided to extend along the longitudinal axis X. A distal end of the guide tube 77 is connected to the support member 51 of the base portion 27.

A guide channel 78 is formed inside of the guide tube 77. A distal end of the guide channel 78 communicates with the cavity portion 52. In the guide channel 78, a drive shaft 79 that is a linear portion is provided to extend along a shaft axis S.

A rotational driving force that is generated in the motor 72 is transmitted to the drive shaft 79 via the relay gear 75 and the drive gear 76. By the rotational driving force being transmitted to the drive shaft 79, the drive shaft 79 rotates with the shaft axis S as a center.

A distal end of the drive shaft 79 is connected to the drive gear 55 of the driving force transmission unit 53. The drive shaft 79 rotates, whereby the rotational driving force is transmitted to the driving force transmission unit 53, and the driving force transmission unit 53 is driven. The rotational driving force is transmitted to the rotating cylindrical member 58, and thereby the rotational driving force is transmitted to the rotation unit 30 as described above. Thereby, the rotation unit 30 rotates.

Note that as illustrated in FIG. 5, inside of the insertion portion 3, bending wires 38A and 38B are provided to extend along the longitudinal axis X. Inside the operation portion 5, proximal ends of the bending wires 38A and 38B are connected to a pulley (not illustrated) connected to the bending operation knob 37.

Distal ends of the bending wires 38A and 38B are connected to a distal end portion of the bending portion 22. By bending operation on the bending operation knob 37, the bending wire 38A or the bending wire 38B is pulled, and the bending portion 22 bends. Note that in the present embodiment, the bending portion 22 is configured by only an active bending portion that bends by a bending operation.

The respective bending wires 38A and 38B are inserted through corresponding coils 39A and 39B. Proximal ends of the coils 39A and 39B are provided to extend to the inside of the operation portion 5. Distal ends of the coils 39A and 39B are connected to an inner peripheral surface of a distal end portion of the first flexible tube portion 23. Note that in the present embodiment, the two bending wires 38A and 38B are provided, and the bending portion 22 is bendable in two directions. However, for example, four bending wires may be provided, and the bending portion 22 may be bendable in four directions.

As illustrated in FIG. 6, in the endoscope 2 of the present embodiment, the first flexible tube portion 23 and the second flexible tube portion 25 are formed of a first spiral tube 91 that is a first flex tube, a first flexible net-shaped tube 92 that is a first flexible braid tube, and a first flexible outer sheath 93 that is an outer sheath tube.

The first spiral tube 91, the first flexible net-shaped tube 92 and the first flexible outer sheath 93 are provided to extend along the longitudinal axis X from the distal end of the first flexible tube portion 23 to a proximal end of the second flexible tube portion 25.

An outer peripheral direction side of the first spiral tube 91 is covered with the first flexible net-shaped tube 92, and an outer peripheral direction side of the first flexible net-shaped tube 92 is covered with the first flexible outer sheath 93.

The first spiral tube 91 includes a metal band-shaped member. In the first spiral tube 91, a band-shaped member 95 is provided to extend spirally around the longitudinal axis X.

The first flexible net-shaped tube 92 includes a metal element wire. In the first flexible net-shaped tube 92, an element wire 96 is woven. The first flexible outer sheath 93 is formed from a resin material.

A proximal end portion of the bending tube 81 is fitted to a cylindrical connection tube 84 (refer to FIG. 3), and the first spiral tube 91 and the first flexible net-shaped tube 92 are fitted to the connection tube 84 in a state where the first spiral tube 91 and the first flexible net-shaped tube 92 are inserted in an inner peripheral direction side of the connection tube 84.

The first flexible outer sheath 93 is bonded to the bending outer sheath 85 via an adhesive portion 86 such as an adhesive. As described above, the first flexible tube portion 23 and the bending portion 22 are connected. The first spiral tube 91, the first flexible net-shaped tube 92, and the first flexible outer sheath 93 are fitted to the support member 51 in a state where the first spiral tube 91, the first flexible net-shaped tube 92, and the first flexible outer sheath 93 are inserted in the inner peripheral direction side of the support member 51 as illustrated in FIG. 4.

Thereby, the second flexible tube portion 25 is connected to the base portion 27. In the present embodiment, the first spiral tube 91, the first flexible net-shaped tube 92, and the first flexible outer sheath 93 are provided to extend in a state of continuing between the first flexible tube portion 23 and the second flexible tube portion 25.

Note that the third flexible tube portion 26 is formed of a second spiral tube 101 that is a second flex, a second flexible net-shaped tube 102 that is a second flexible blade, and a second flexible outer sheath 103 (refer to FIG. 4).

The second spiral tube 101, the second flexible net-shaped tube 102, and the second flexible outer sheath 103 are provided to extend along the longitudinal axis X from a distal end of the third flexible tube portion 26 to a proximal end of the third flexible tube portion 26. An outer peripheral direction side of the second spiral tube 101 is covered with the second flexible net-shaped tube 102, and an outer peripheral direction side of the second flexible net-shaped tube 102 is covered with the second flexible outer sheath 103.

A proximal end portion of the support member 51 is fitted to the connection member 104. The second spiral tube 101 and the second flexible net-shaped tube 102 are fitted to the connection member 104 in a state where the second spiral tube 101 and the second flexible net-shaped tube 102 are inserted in an inner peripheral direction side of the connection member 104 (refer to FIG. 4). Thereby, the third flexible tube portion 26 is connected to the base portion 27.

In the second spiral tube 101, a metal band-shaped member is provided to extend in a spiral shape with the longitudinal axis X as a center. In the second flexible net-shaped tube 102, a metal element wire is woven. The second flexible outer sheath 103 is formed from a resin material.

Here, a configuration of the spiral tube 31 will be described in detail below. As illustrated in FIG. 6, in the spiral tube 31, a tube portion 32 that occupies most part includes a covering tube 201 as a jacket that is an outer layer tube body, and a corrugated tube 202 that is an inner layer tube body. In other words, in the tube portion 32, an outer periphery of the corrugated tube 202 is covered with the covering tube 201.

In the covering tube 201, a spiral fin 33 that is a spiral protruded portion of a resin such as polyvinyl chloride is spirally provided on an outer peripheral surface of a resin tube such as polyvinyl chloride by an adhesive. Note that the corrugated tube 202 is a so-called bellows tube formed from low-density polyethylene or the like and having a plurality of grooves 208 in a peripheral direction.

Entire bending rigidity of the tube portion 32 is set by the covering tube 201 and the corrugated tube 202. In this way, the tube portion 32 of the spiral tube 31 is a very soft tube body with the covering tube 201 put on the corrugated tube 202.

In the covering tube 201, a distal end portion is fixed to the distal end side cylindrical portion 35 as a first cylindrical member by bonding or the like. In the corrugated tube 202, a proximal end portion is fixed to the proximal end side cylindrical portion 36 as a second cylindrical member by bonding or the like.

Note that such a configuration may be adopted that a proximal end portion of the covering tube 201 is fixed to the proximal end side cylindrical portion 36 by bonding or the like, and a distal end portion of the corrugated tube 202 is fixed to the distal end side cylindrical portion 35 by bonding or the like.

The tube portion 32 is of a two-layer tube structure in which the covering tube 201 only covers the corrugated tube 202, and is not fixed to the corrugated tube 202. In other words, the covering tube 201 is slidable back and forth between a distal end side and a proximal end side along the longitudinal axis X on an outer peripheral portion of the corrugated tube 202.

In the tube portion 32, a sliding range restriction portion 200 is provided in the proximal end portion. The sliding range restriction portion 200 is provided in the covering tube 201 and configures a holding portion that prevents the corrugated tube 202 from falling off. The sliding range restriction portion 200 also configures a positioning portion that defines a moving range in which the covering tube 201 slides with respect to the corrugated tube 202.

Describing in detail, as illustrated in FIG. 7, in the corrugated tube 202, first recessed and protruded portions 204 with a predetermined height are formed throughout a substantially entire length except for a position of the sliding range restriction portion 200, and the corrugated tube 202 is set to have predetermined flexibility.

In a range of the sliding range restriction portion 200, the corrugated tube 202 has two protruded portions 205 that protrude in an outside diameter direction by a predetermined height h1 from an outer peripheral portion of the first recessed and protruded portion 204, and separate in a direction along the longitudinal axis X so that a groove width of a predetermined distance D is formed.

The corrugated tube 202 has second recessed and protruded portions 206 that are formed between the two protruded portions 205 to be recessed in an inside diameter direction by a predetermined height h2 from the outer peripheral portion of the first recessed and protruded portion 204.

Thereby, in the corrugated tube 202 in the sliding range restriction portion 200, a recessed portion 207 in a circumferential groove shape of a predetermined distance D between the two protruded portions 205 is formed.

In the covering tube 201, an inner peripheral surface of a ring member 203 as a proximal ring is bonded to an outer peripheral surface of the covering tube 201 in the range of the sliding range restriction portion 200, which covers the recessed portion 207 of the corrugated tube 202. The ring member 203 is formed from polyvinyl chloride or the like, and has a predetermined length L in a direction along the longitudinal axis X.

Note that in the ring member 203, a width of the predetermined length L is set so that a distal end surface separates from the distal end side protruded portion 205 of the corrugated tube 202 with a predetermined distance d. Note that the predetermined distance d is set at substantially 2 to 3 mm.

The ring member 203 here is provided to hold down the covering tube 201 in an inside diameter direction so that the covering tube does not exceed the protruded portion 205 at the distal end side. In the present embodiment, a proximal end of the spiral fin 33 is bonded to an outer peripheral surface of the ring member 203. Note that the proximal end of the spiral fin 33 does not necessarily have to be bonded to the ring member 203.

In the spiral tube 31 that is configured in this way, two protrusion portions a and b are formed in a proximal end part of the tube portion 32, and the ring member 203 is provided in a circumferential groove c in a recessed portion shape formed by the two protrusion portions a and b.

In this way, the spiral tube 31 of the present embodiment is configured such that the two layers of the covering tube 201 that is the outer sheath, and the corrugated tube 202 covered with the covering tube 201 are not completely fixed, and the covering tube 201 is made slidable to the corrugated tube 202.

Thereby, the spiral tube 31 easily bends without the covering tube 201 being stretched, and even in a state where the first flexible tube portion 23 of the insertion portion 3 of the endoscope 2 bends, sliding resistance of an inner peripheral surface of the spiral tube 31 and an outer peripheral surface of the first flexible tube portion 23 is reduced.

More specifically, as illustrated in FIG. 8, even when the covering tube 201 of the tube portion 32 is pulled to the distal end side (arrow F direction) along the longitudinal axis X from the state illustrated in FIG. 7, the ring member 203 moves to the distal end side within the range of the sliding range restriction portion 200, so that the covering tube 201 is not stretched, a tensile force decreases, and the spiral tube 31 easily bends.

In other words, when the spiral tube 31 bends, a tensile force by which the covering tube 201 at a bending outer side is pulled and stretched occurs. However, the covering tube 201 slides to a front side that is the distal end side with respect to the corrugated tube 202, and thereby can reduce the tensile force, so that the spiral tube easily bends.

Note that when the spiral tube 31 returns from the bending state to a rectilinear state, the covering tube 201 that is pulled to the distal end side (arrow F direction) moves to the proximal end side (arrow B direction) along the longitudinal axis X and slides.

As a result, the sliding resistance between the inner peripheral surface of the spiral tube 31 and the outer peripheral surface of the insertion portion 3 decreases, and the spiral tube 31 can ensure stable rotatability. Accordingly, the spiral tube 31 can be configured to be able to rotate smoothly even in a state where the insertion portion 3 of the endoscope 2 bends and obtain stable rotatability.

As a configuration for the above, in the spiral tube 31, only the one end of each of the covering tube 201 and the corrugated tube 202 is fixed, because sliding cannot be performed when both ends of each of the covering tube 201 that is an outer layer and the corrugated tube 202 that is an inner layer tube are fixed.

In other words, the covering tube 201 and the corrugated tube 202 are configured so that the end portions at opposite sides to each other are fixed, because the covering tube 201 cannot slide with respect to the corrugated tube 202 if both the covering tube 201 and the corrugated tube 202 are configured such that end portions at the same sides (for example, only distal ends of both of them, or only proximal ends of both of them) are fixed.

In the spiral tube 31, the ring member 203 is provided in the circumferential groove c in the recessed portion shape in the sliding range restriction portion 200 formed on the outer peripheral portion. Thereby, even when the spiral fin 33 provided on the outer peripheral surface of the covering tube 201 receives a load in the longitudinal X direction due to resistance between the spiral fin 33 and a wall portion of a subject, the ring member 203 is caught by the protrusion portion a of the sliding range restriction portion 200. Therefore, the corrugated tube 202 is prevented from falling off from the covering tube 201.

With rotation followability taken into consideration, it is necessary that the outer rollers 65A to 65F that are driving force receiving portions are connected to the corrugated tube 202. Since the outer rollers 65A to 65F are attached to the proximal end side cylindrical portion 36 at the proximal end side, the length of the drive shaft 79 is shortened, and the spiral tube 31 has an advantage of improving in the rotation transmission efficiency.

(First Modification)

Figure 9:
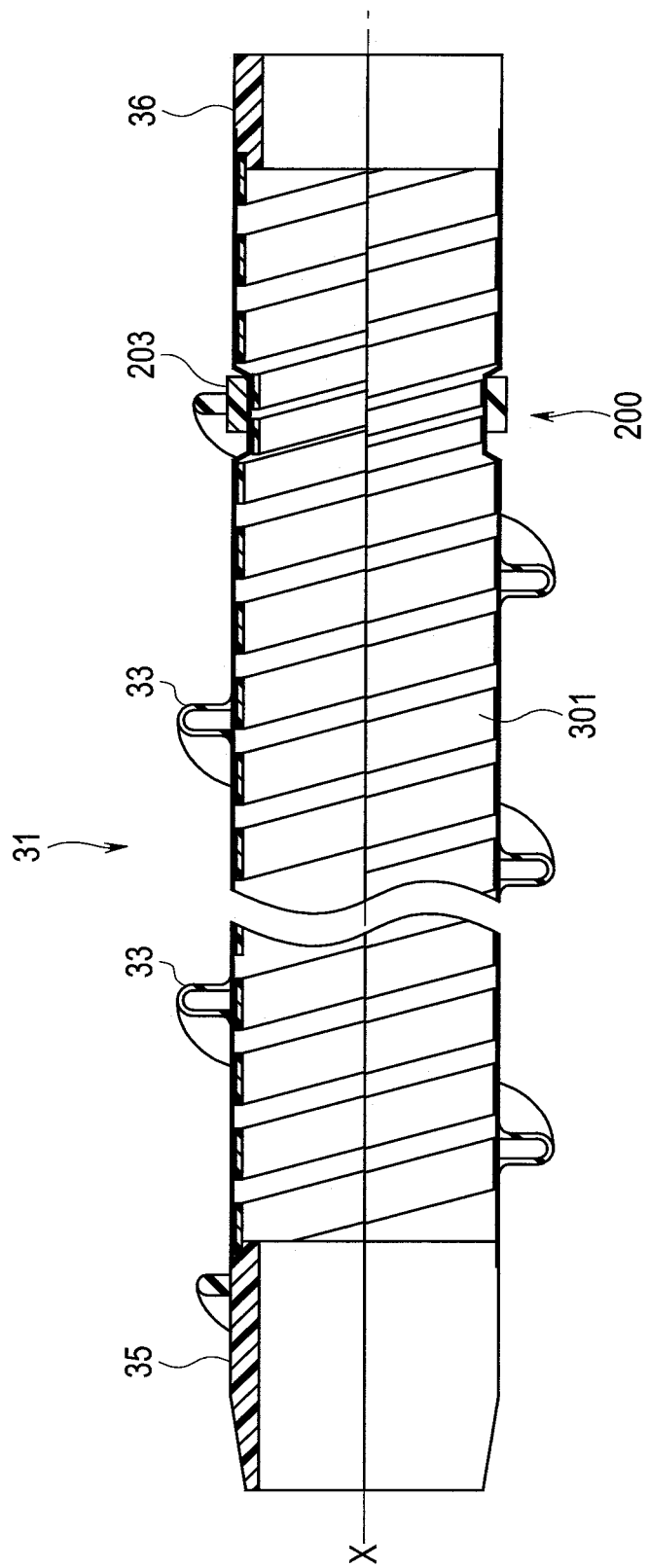
FIG. 9 is a sectional view illustrating a configuration of a spiral tube of a first modification, according to one aspect of the present invention.

FIG. 9 is a sectional view illustrating a configuration of a spiral tube of a first modification.

As illustrated in FIG. 9, an inner layer tube of a spiral tube 31 may be a spiral sleeve 301 formed by winding a band-shaped body spirally, instead of the corrugated tube 202.

(Second Modification)

FIG. 10 is a sectional view illustrating a configuration of a spiral tube of a second modification.

As illustrated in FIG. 10, an inner layer tube of a spiral tube 31 may be a cylindrical flexible tube body 302 formed from a superelastic alloy material such as Ni—Ti (nickel titanium) in which a plurality of slots 303 are formed in a cylindrical body, instead of the corrugated tube 202.

Note that the present invention is not limited to only the embodiment described above, but can be carried out by being variously modified within the range without departing from the gist of the invention.

According to the present invention, it is possible to realize the spiral tube that is enabled to rotate smoothly even in the state where the insertion portion of the endoscope bends to obtain stable rotatability and the endoscope.

What is claimed is:

1. A spiral tube for use on an outer peripheral portion of an insertion portion of an endoscope configured to be inserted into a subject, and rotatable around an insertion axis of the insertion portion by a driving force of a driving unit, the spiral tube comprising:
    a first cylindrical member provided at one end;
    a second cylindrical member provided at an other end;
    a tube comprising:
        an inner layer tube that has one end fixed to the second cylindrical member, and the inner layer tube is elongated along a longitudinal axis; and
        an outer layer tube that has one end fixed to the first cylindrical member, the outer tube layer is elongated along the longitudinal axis, the outer tube layer covering an outer periphery of the inner tube layer and is slidable relative to the inner tube layer in a longitudinal direction; and
    s sliding range restriction portion provided at an other end side of the outer layer tube, and configured to restrict movement of the outer layer tube relative to the inner layer tube to a predetermined range and to hold the inner layer tube in the outer layer tube, the sliding range restriction portion comprising:
        the tube having a circumferential groove inwardly recessed in a radial direction relative to other portions of the tube; and
        a ring member provided in the circumferential groove a portion of the outer layer tube corresponding to the circumferential groove.

2. The spiral tube according to claim 1, wherein the ring member is fixed to the outer layer tube, moves with the outer layer tube within a range along the longitudinal axis of the circumferential groove of the inner layer tube, and restricts a moving range of the outer layer tube with respect to the inner layer tube.

3. The spiral tube according to claim 1, wherein
    the inner layer tube is a corrugated tube with recesses and protrusions formed on an outer peripheral portion, and
    the circumferential groove is formed by making a height of the protrusions of the corrugated tube corresponding to the circumferential groove lower than a height of the protrusions in portions of the corrugated tube other than the circumferential groove.

4. The spiral tube according to claim 3, wherein the height of the protrusions of the corrugated tube at each end of the corrugated tube adjacent to the circumferential groove are higher in an outside diameter direction than the height of protrusions of the corrugated tube corresponding to the circumferential groove.

5. The spiral tube according to claim 1, wherein
    the first cylindrical member is provided at a distal end,
    the second cylindrical member is provided at a proximal end, and includes a driving force receiving member to receive the driving force,
    the inner layer tube has a proximal end of the inner layer tube fixed to the second cylindrical member,
    the outer layer tube has a distal end of the outer layer tube fixed to the first cylindrical member, and
    the sliding range restriction portion is provided closer to a proximal end of the outer layer tube than to the distal end of the outer layer tube.

6. The spiral tube according to claim 1, further comprising a spiral fin provided on an outer periphery of the outer layer tube, and the spiral fin is formed to protrude spirally from the outer periphery.

7. An endoscope, comprising the spiral tube according to claim 1.

* * * * *